United States Patent
Stieglitz et al.

[11] Patent Number: 5,919,220
[45] Date of Patent: Jul. 6, 1999

[54] CUFF ELECTRODE

[75] Inventors: Thomas Stieglitz, Pirmasens; Joerg-Uwe Meyer, St. Ingbert, both of Germany

[73] Assignee: Fraunhofer Gesellschaft zur Foerderung der angewandten Forschung e.V.

[21] Appl. No.: 08/809,190
[22] PCT Filed: Sep. 8, 1995
[86] PCT No.: PCT/EP95/03545
§ 371 Date: Mar. 17, 1997
§ 102(e) Date: Mar. 17, 1997
[87] PCT Pub. No.: WO96/08290
PCT Pub. Date: Mar. 21, 1996

[30] Foreign Application Priority Data

Sep. 16, 1994 [DE] Germany ............................. 44 33 111

[51] Int. Cl.[6] ............................................. A61N 1/05
[52] U.S. Cl. ........................................... 607/118; 600/377
[58] Field of Search .............................. 607/118; 600/377

[56] References Cited

U.S. PATENT DOCUMENTS

| | | |
|---|---|---|
| 3,654,933 | 4/1972 | Hagfors . |
| 3,738,368 | 6/1973 | Avery et al. . |
| 3,774,618 | 11/1973 | Avery . |
| 3,955,560 | 5/1976 | Stein et al. . |
| 4,940,065 | 7/1990 | Tanagho et al. ..................... 607/118 |
| 5,282,468 | 2/1994 | Klepinski ............................ 600/377 |
| 5,344,438 | 9/1994 | Testerman et al. .................. 607/118 |
| 5,476,494 | 12/1995 | Edell et al. ......................... 607/118 |

FOREIGN PATENT DOCUMENTS

| | | |
|---|---|---|
| 0 408 358 | 1/1991 | European Pat. Off. . |
| WO 87/07825 | 12/1987 | WIPO . |
| WO 91/17791 | 11/1991 | WIPO . |
| WO 93/20887 | 10/1993 | WIPO . |

OTHER PUBLICATIONS

"Selective Control of Muscle Activation with a Multipolar Nerve Cuff Electrod" in *IEEE Transactions on Biomedical Engineering*, vol. 40, No. 7, Jul. 1993 by Claude Veraart et al.

"Mikrofertigung mit Methoden der Halbleitertechnologie" in *Mikromechanik*, Springer–Verlag Berlin, Heidelberg, New York, London, Paris, Tokyo 1989.

*Primary Examiner*—Lee Cohen
*Attorney, Agent, or Firm*—Evenson, McKeown, Edwards & Lenahan, P.L.L.C.

[57] ABSTRACT

The present invention relates to a cuff-electrode that can be placed as an extraneural, sleeve-shaped electrode about a biological tissue, e.g. a nerve.

15 Claims, 2 Drawing Sheets

CUFF ELECTRODE

FIELD OF THE INVENTION

The present invention relates to a cuff electrode and, more particularly, to a cuff-electrode which can be placed in the manner of an extraneural, sleeve-shaped electrode about a biological tissue, e.g., a nerve. Raised electrodes are provided on a foil of various layers of non-conductive material. The individual electrodes are contacted via strip conductors. The strip conductors are disposed between the non-conducting layers. At least one of the non-conducting layers is composed of a shape memory material or stands under mechanical pretension to ensure the cuff-shaped structure. Such a cuff-shaped electrode is known, e.g. from WO 91/17791.

Furthermore, reference is made to the article "Selective Control of Muscle Activation with a Multipolar Nerve Cuff Electrode" in IEEE Transactions on Biomedical Engineering, Vol. 40, No. 7, Jul. 1993, as well as to U.S. Pat. Nos. 4,750,499; 5,038,781; and 5,324,322 for further details of cuff electrodes.

The technical field of the new flexible interdigital cuff electrodes (FLIC) is in neuroprosthesis. New possibilities are being sought in this field for the long term gentle contact of bundles of nerves with a multiplicity of electrodes. Utilization of technical assistance systems in human bodies should permit, by means of registering nerve signals and by means of stimulation, the reproduction and/or imitation of failed body functions.

BACKGROUND OF THE INVENTION

Drawbacks of the State of the Art
A. Rigid Cuff Electrodes

Extraneural, cuff-like electrodes, so called "cuff electrodes" which are placed circularly around the nerve, have been a part of successful biomedical electrodes on the market since the end of the 1970s. There are a number of US patents for rigid construction, so-called "split cylinder", cuff electrodes: U.S. Pat. No. 3,774,618; U.S. Pat. No. 3,738,383; and U.S. Pat. No. 3,654,933. Some implanted electrodes have been in safe use for 15 years. Their disadvantages were, and still are, their limited selectivity due to the small number of electrodes (circular maximum 4). The arrangement of three electrodes in the longitudinal direction of the cuff, and the use of transverse control currents, permits improving the selectivity and stimulation of deeper lying parts of nerves. However, their relatively rigid form may damage the nerves in the event of post-operative edematous swelling due to the pressure of the electrode on the nerves. If the diameter of the cuff is selected to be larger, then conduction and stimulation conditions are considerably impaired due to the ingrowing of the tissue.

B. Flexible Cuff Electrodes

The introduction of the so-called spiral cuff electrodes constituted an approach to reduce postoperative increases in pressure. In this mode of construction, a prestretched silicon foil is connected to an unstretched foil using a medical silicon adhesive. The electrodes are composed of platinum wires which are placed between the foils. The active electrode surfaces are created by opening windows (using, for example, a scalpel or punching iron) in the prestretched foil.

Due to the tensile stress of the prestretched foil, the electrode curls, thus becoming a spiral. When the nerves swell, the spiral-shaped cuff electrode can stretch and thereby partially compensate for the increase in pressure.

C. Helix Electrodes

The term helix electrode refers to electrodes that are wound screw-like around the nerve. They are employed in monopolar and bipolar form with a maximum of two electrodes. Due to the open construction of the electrode, the danger of the pressure damaging the nerves by swelling is minimal. However, field definition on the interior of the electrode when stimulated (less energy needs) is not possible. The helix electrodes disadvantageously have no way of selectively stimulating specific parts of the nerve cross section.

The object of the present invention is to provided an improved cuff electrode. In particular, the object is to reduce the pressure placed on the nerves by the electrode. A bidirectional coupling to the nerves with high spatial and temporal resolution has the purpose of permitting diversion of the nerve signals and/or electric stimulation of nerve fibers.

SUMMARY OF THE INVENTION

This object is solved according to the present invention by a cuff-electrode which can be placed in the manner of an extraneural, sleeve-shaped electrode about a biological tissue, e.g., a nerve. Raised electrodes are provided on a foil of various layers of non-conductive material. The individual electrodes are contacted via strip conductors. The strip conductors are disposed between the non-conducting layers. At least one of the non-conducting layers is composed of a shape memory material or stands under mechanical pretension to ensure the cuff-shaped structure. The layers of material having said electrodes are designed to be finger-shaped such that they lie snugly next to each other in a nerve embracing state. A multiplicity of rod-shaped electrodes are provided in an array arrangement such that the load pressure on the nerves is minimal.

Using raised electrodes according to the invention reduces the effective contact surface in such a manner that the "negative pressure" of a dot construction is generated leading to improved biocompatability and to improved fixation of fibroids. The new cuff construction permits field definition to the electrode interior by means of which the required amount of energy for stimulation is kept low. The high number of electrodes permits a high spatial and temporal resolution and the use of tripolar arrangements in order to concentrate the electric field and the use of transversal control currents for excitation of deeper nerve structures. For further details on this, reference is made to the aforecited publication IEEE transaction 1993.

The finger structure pursues two goals: first, in the event of edematous swelling, the pressure of the electrode on the nerves is reduced. This is because single strips or "fingers" can adapt to nonuniform swelling.

Contrary to conventional cuff electrodes, the physiological irregularities of the nerves are taken into account. Secondly, the structure permits diffusion of the metabolic products through the spaces between the fingers which can have a positive effect in a postoperative regeneration phase. This is because the toxic metabolic end products can be carried away. This is also achieved by the raised electrodes and the intermediate spaces between the raised electrodes.

The use of flexible interdigital cuff electrodes (FLIC) is planned at the peripheral nerves and in the marrow of the spinal cord. An epidural and subdural implantation about the spinal cord marrow is feasible. In the event of an implantation about the spinal cord marrow, following a laminectomy, two FLICs are placed radially about the spinal cord marrow between two roots.

The present invention creates the following improvements and advantages in comparison to the state of the art: high temporal-spatial resolution; permits adaption of the radius of the electrode to the irregularities along the nerves due to the interdigital structure; reduces the pressure on the nerves in the case of local post-operative edematous swelling; and improves biocompatability due to raised electrodes, i.e., a reduction of the active contact surface.

DETAILED DESCRIPTION OF THE DRAWINGS

Figure 1:
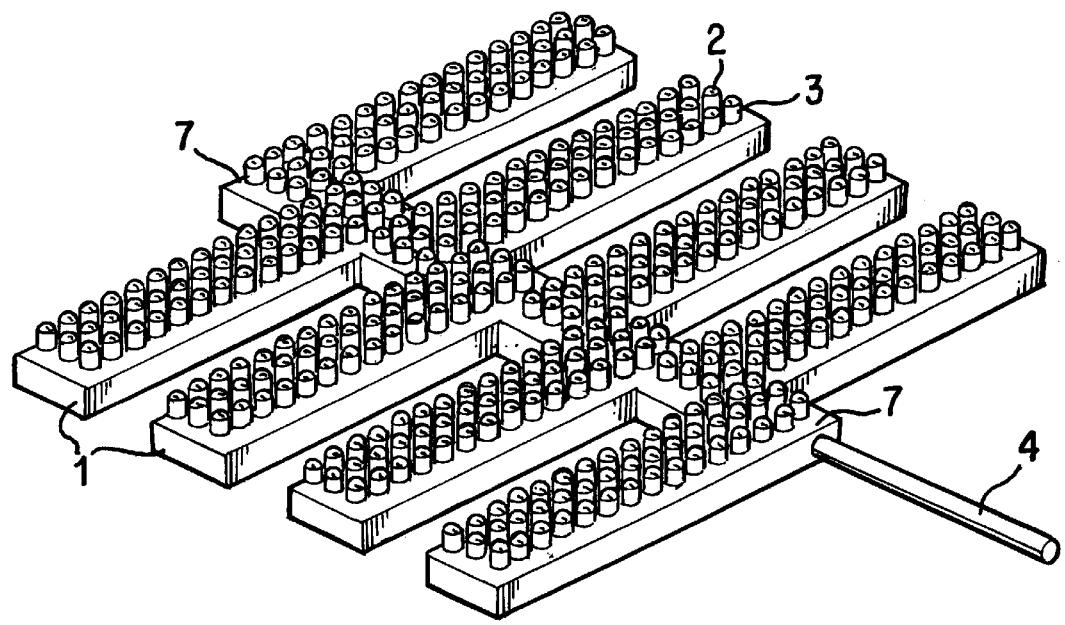
FIG. 1 is a perspective representation of a cuff electrode according to the present invention in an unrolled state.
Figure 2:
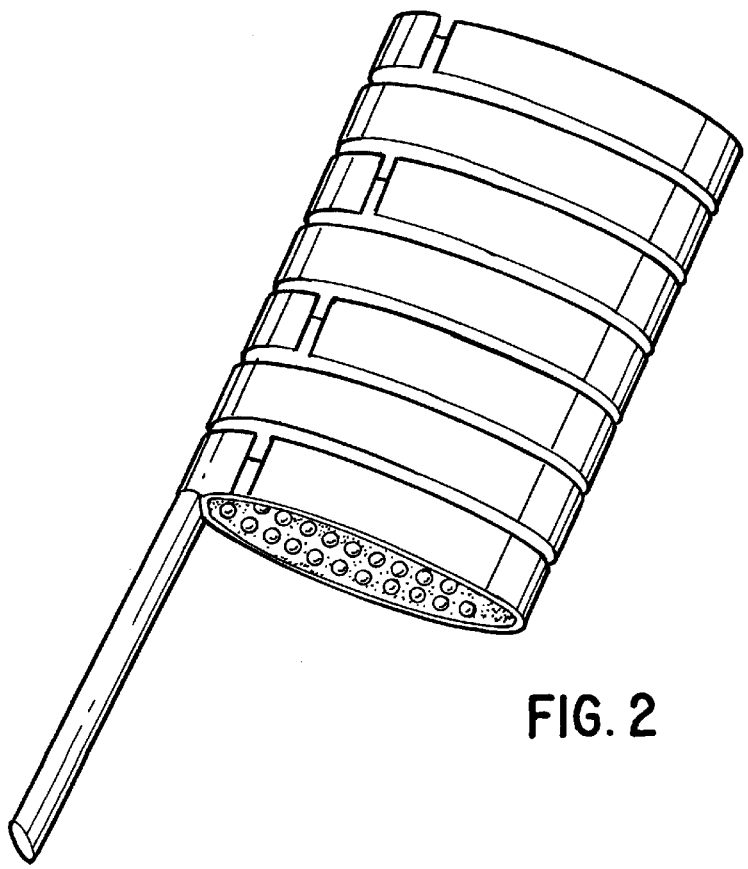
FIG. 2 is perspective representation of a cuff electrode according to the invention in a curled state.
Figure 3:
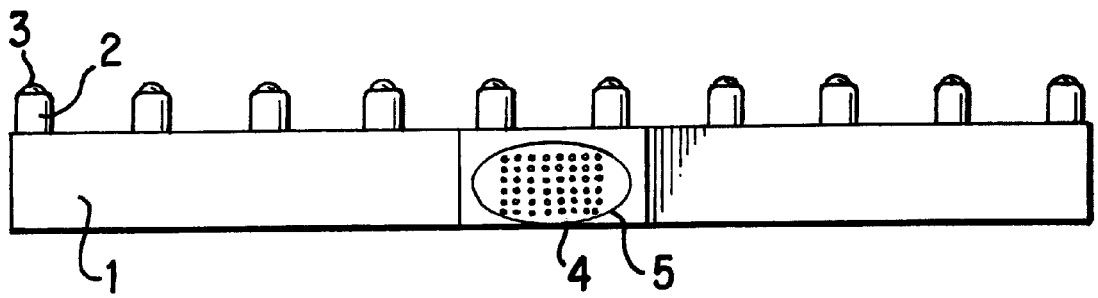
FIG. 3 is a schematic section view of a cuff electrode according to the invention.
Figure 4:
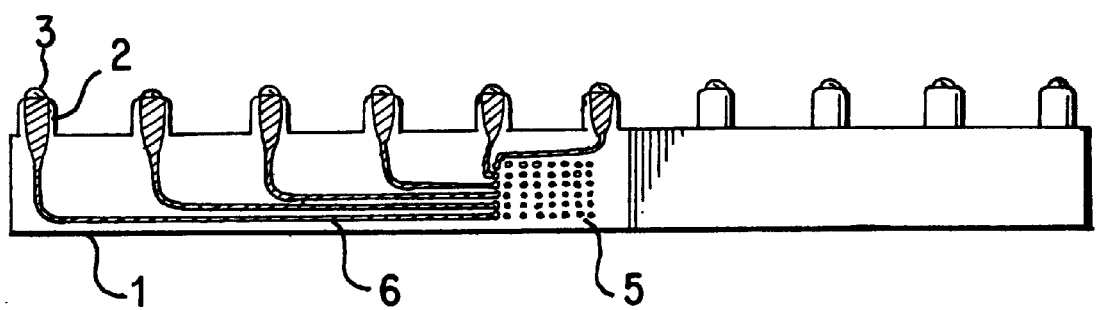
FIG. 4 is a schematic section view of a cuff electrode according to the present invention.

The present invention is shown schematically in a perspective representation in FIGS. 1 and 2, and in FIGS. 3 and 4 in a section view. FIG. 1 shows the flexible interdigital cuff (FLIC) electrode in a planar state and FIG. 2 shows the cuff electrode in a curled form, with the nerve coming to lie inside the curled finger. The nerve is not depicted in the figure. FIG. 3 shows a lateral view of the FLIC electrode in a planar state (a view of the cutting edge of the connecting cable). FIG. 4 shows a sectional drawing of the FLIC electrode in a planar state (a section of the first electrode finger).

The FLIC is composed of a flexible, multilayer substrate in finger structure 1 of non-conducting silicon, on which are located raised electrodes 3 of conductive silicon. The strip conductors 5 leading to the electrodes 3 run between the non-conducting layers of the finger and are also composed of conductive silicon. These conductors are shown in FIGS. 3 and 4 only for 48 electrodes, because the depicted 45 electrodes per finger according to FIG. 1 is difficult to depict in a drawing. The cuff electrode according to FIGS. 3 and 4 has 6 electrodes per finger, with 4 fingers on the left side and 4 fingers on the right side. The strip conductors 5 and electrodes are created by means of microstructural molding using negative forms made with conventional silicon technology, e.g., forms are provided in which the silicon rubber is spread (put), which is subsequently thermically cross-linked. Both wet-chemically etched structures in silicon can serve as forms, cf., e.g., Anton Heuberger Micromechanik "Mikrofertigung mit Methoden der Halbleitertechnologie", Springer-Verlag Berlin, Heidelberg, New York, London, Paris, Tokyo 1989, and forms made by precision mechanics.

The rolled up shape of the FLIC is produced by setting various prestress in the multilayer buildup or by utilizing shape memory alloys or by electrochemical actuators. Shape memory alloys are inserted into the layers of insulating material in the form of single strips. As the prestress needs to be relatively small, one layer of shape memory material suffices. The shape memory alloy is surrounded on all sides by insulating silicone rubber 1 and has no contact with the conducting structures of electrodes 3 and feed lines 5, 6. The electrodes with the feed lines in the fingers and the lead 4 are insulated against each other and are connected to a processing unit (not shown) for applying stimulating currents to the electrodes. The lines 5, 6 can be arranged in a circuit such that diversions of the nerve signals can also be received in the processing unit.

The strip conductors 5, 6 and electrodes 3 are preferably made of conductive silicone rubber in a microstructure technique. This is true also for the insulating silicon layers lying inbetween them. Employing silicon foils is not foreseen. Reference number 3 denotes the active electrode structure made of conductive silicone rubber. Subsequent electroplating, e.g., galvanic precipitation of carbon, gold, platinum or iridium onto the "tips" depicted in FIG. 3, can occur as a modification for reducing the electrode transition impedance (improved signal-to-noise ratio in the derivations). Precipitation of platinum and/or iridium increases the charge amount that can be applied per stimulation impulse per electrode by means of reversible electrochemical processes.

FIGS. 3 and 4 show the raised electrode structure having a basic material of non-conducting silicone rubber 2. The non-conducting silicone rubber 2 lies like a sheath around the conducting core and permits electric insulation of the individual electrodes 3 from each other (see FIG. 4).

The right side of FIG. 4 is not depicted as a section, because the second electrode finger, which is offset to the back to the first one, can already be seen in it.

The non-conducting silicone rubber provides the carrier structure for the feed lines 6 and supports them mechanically. It also insulates the individual feed lines 5, 6 in the connection cable 4.

According to FIGS. 1–4, the raised electrodes are designed in a rod-shape with a hemispherical electrode tip. The rod-shaped electrodes have a height above a surface of the substrate greater than a width of an electrode contact surface of the rod-shaped electrodes. They can, of course, also be little rods with a square or polygonal cross section, or also with a rounded tip. This design considerably reduces the effective contact areas of the cuff electrode with the nerves yielding a dot-shaped grid on the nerve tissue. Due to the impression in the tissue, the dots have a two-dimensional shape. Graphically seen, the cavities between the raised structure form a grid or network. Due to the finger structure, the individual fingers can lay around the nerves with a varying average diameter adapted to the nerves.

The number of electrodes used can fluctuate according to the type of application. Preferable are, in any event, multiple electrodes per finger, e.g., 4–50 electrodes per finger. The number of fingers also depends on the type of application and the thickness of the nerve. Foreseen are, e.g., at least two fingers per side, i.e., on the whole four fingers, but preferably 4–5 or more fingers per side.

According to FIGS. 1 and 2, the fingers to the left and right of a center part 7 are disposed with 4 fingers on each side. Other arrangements of the fingers about a central part are, of course, also contemplated. Thus, for instance, all of the fingers may be disposed on only one side and then embrace the nerves like a hand. Or, for example, two fingers each may lay side by side and on the other side a corresponding empty space. In the most simple case, it suffices if there is only one finger on one side and two fingers on the other side with an intermission space for one finger analogously to FIG. 1 or, as indicated above, with 3 fingers along the central part 7 on the same side.

Preferred Embodiment

Along the longitudinal axis of the flexible interdigital cuff electrode are located on each side of a center fillet 4 to 6 "fingers" having 6–45 raised electrodes, which may be of any desired configuration, in order to be able to utilize the same FLIC in principle both for the diversion of electro-neurograms (ENG) and for stimulation. The possible dimensions of the FLIC are approximately 10 mm in length with an approximately 1.4 mm–40 mm diameter.

What is claimed is:

1. A cuff-electrode which is placed around a biological tissue as an extraneural, sleeve-shaped electrode, comprising:

layers of non-conductive material having provided thereon raised electrodes, individual ones of said raised electrodes being contacted via strip conductors disposed between the layers of non-conductive material;

wherein at least one of the layers of non-conductive material is ensured a cuff-shaped form via one of mechanical pretensioning and use of a shaped memory material; and wherein said layers of non-conductive material having said raised electrodes thereon are designed in a finger-shape such that fingers thereof lie snugly next to one another in a nerve embracing state of the cuff electrode, said raised electrodes being rod-shaped electrodes provided in an arrayed arrangement on said fingers such that a load pressure on the biological tissue is minimal.

2. The cuff-electrode according to claim 1, wherein approximately 4 to 50 electrodes are provided per finger, said rod-shaped electrodes having one of a round and polygonal cross-section and a spherically shaped electrode tip, said rod-shaped electrodes being made of a conductive silicon.

3. The cuff-electrode according to claim 2, wherein 6 to 20 electrodes are provided per finger.

4. The cuff-electrode according to claim 1, further comprising a feed cable coupling to the rod-shaped electrodes, wherein said rod-shaped electrodes, said strip conductors, and said feed cable are formed via microstructural molding using negative molds.

5. The cuff-electrode according to claim 1, wherein said rod-shaped electrodes are disposed such that a high time-space resolution is obtained both for a stimulation of nerves and a diversion of nerve signals such that tripolar electrode circuits having transverse control currents are designed.

6. The cuff-electrode according to claim 1, wherein electrode tips of said rod-shaped electrodes form contact areas and are coated with one of platinum, iridium and iridium oxide.

7. The cuff-electrode according to claim 1, wherein said shaped memory material is made of one of metal and plastic, and wherein said mechanical pretensioning is provided by one of a spring steel and resilient plastic.

8. The cuff-electrode according to claim 1, wherein at least two fingers are provided per side, said two fingers being disposed to the left and the right of a central piece such that said fingers engage in the nerve embracing state.

9. The cuff-electrode according to claim 8, wherein 3 to 5 fingers are provided per side.

10. The cuff-electrode according to claim 1, wherein said rod-shaped electrodes are defined such that a longitudinal length of said rod-shaped electrodes is greater than a transverse length through an electrode contact surface of said rod-shaped electrodes.

11. The cuff-electrode according to claim 1, wherein a height of said rod-shaped electrodes above a surface of said fingers is greater than a width of an electrode contact surface of said rod-shaped electrodes.

12. A cuff-electrode for placement about a nerve as an extraneural, sleeve-shaped electrode, comprising:

a multilayer substrate having a plurality of individual fingers;

a multiplicity of rod-shaped electrodes provided in an array form on said individual fingers, each of said multiplicity of rod-shaped electrodes having a height above a surface of the substrate greater than a width of an electrode contact surface;

strip conductors disposed between the multilayer substrate for coupling with each of said rod-shaped electrodes;

wherein said fingers are arranged such that in a curled state of said sleeve-shaped electrode, the fingers are closely arranged next to one another; and wherein said array form of the rod-shaped electrodes minimizes a load pressure on the nerve when contacted by the electrode contact surfaces.

13. The cuff-electrode according to claim 12, wherein approximately 4 to 50 electrodes are provided per finger, said rod-shaped electrodes having one of a round and polygonal cross-section and a spherically shaped electrode tip, said rod-shaped electrodes being made of a conductive silicon.

14. The cuff-electrode according to claim 13, wherein 6 to 20 electrodes are provided per finger.

15. The cuff-electrode according to claim 12, wherein at least two fingers are provided per side, said two fingers being disposed to the left and the right of a central piece such that said fingers engage in the nerve embracing state.

* * * * *